United States Patent
Caponigro et al.

(10) Patent No.: US 11,406,627 B2
(45) Date of Patent: Aug. 9, 2022

(54) COMBINATIONS OF MDM2 INHIBITORS WITH INHIBITORS OF ERK FOR TREATING CANCERS

(71) Applicant: NOVARTIS AG, Basel (CH)

(72) Inventors: Giordano Caponigro, Foxborough, MA (US); Ensar Halilovic, Canton, MA (US); Kelli-Ann Monaco, Medford, MA (US)

(73) Assignee: NOVARTIS AG, Basel (CH)

( * ) Notice: Subject to any disclaimer, the term of this patent is extended or adjusted under 35 U.S.C. 154(b) by 8 days.

(21) Appl. No.: 16/754,539

(22) PCT Filed: Oct. 11, 2018

(86) PCT No.: PCT/IB2018/057894
§ 371 (c)(1),
(2) Date: Apr. 8, 2020

(87) PCT Pub. No.: WO2019/073435
PCT Pub. Date: Apr. 18, 2019

(65) Prior Publication Data
US 2020/0281910 A1    Sep. 10, 2020

Related U.S. Application Data

(60) Provisional application No. 62/571,304, filed on Oct. 12, 2017.

(51) Int. Cl.
*A61K 31/4439*    (2006.01)
*A61P 35/00*    (2006.01)
*A61K 31/4965*    (2006.01)

(52) U.S. Cl.
CPC ...... *A61K 31/4439* (2013.01); *A61K 31/4965* (2013.01); *A61P 35/00* (2018.01)

(58) Field of Classification Search
CPC .................................................. A61K 31/4439

USPC ......................................................... 514/338
See application file for complete search history.

(56) References Cited

U.S. PATENT DOCUMENTS

2016/0310476 A1    10/2016    Saurabh et al.

FOREIGN PATENT DOCUMENTS

| WO | 2013/111105 A1 * | 8/2013 |
| WO | 2015/066188 A1 * | 5/2015 |
| WO | 2017/037579 A1 | 3/2017 |

OTHER PUBLICATIONS

Germann et al., AACR Annual Meeting Apr. 18-22, 2015.*
Germann et al., "Targeting the MAPK Signaling Pathway in Cancer: Promising Preclinical Activity with the Novel Selective ERK1/2 Inhibitor BVD-523 (Ulixertinib)," Molecular Cancer Therapeutics, 16(11):2351-2363, 2017.
Wang et al., "Abstract 5466: The Mdm2 inhibitor, NVP-CGM097, in combination with the BRAF inhibitor NVP-LGX818 elicits synergistic antitumor effects in melanoma," Cancer Research, 74(19): 2 pages, 2014.
International Search Report with the International Written Opinion for International Application No. PCT/IB2018/057894, dated Jan. 21, 2019.

* cited by examiner

*Primary Examiner* — Taofiq A Solola
(74) *Attorney, Agent, or Firm* — Scott W. Reid

(57) ABSTRACT

The present invention relates to a pharmaceutical combination comprising (a) an MDM2 inhibitor and (b) an ERK inhibitor, for use in the treatment of a cancer. This invention relates to uses of such combination for preparation of a medicament for the treatment of a cancer; methods of treating a cancer in a subject in need thereof comprising administering to said subject a jointly therapeutically effective amount of said combination; pharmaceutical compositions comprising such combination; and kits and/or packages containing such combinations.

17 Claims, 2 Drawing Sheets

COMBINATIONS OF MDM2 INHIBITORS WITH INHIBITORS OF ERK FOR TREATING CANCERS

This application is an U.S. National Phase filing of International Application Serial No. PCT/IB2018/057894 filed 11 Oct. 2018 and claims priority to U.S. Provisional Application Ser. No. 62/571,304 filed 12 Oct. 2017, both of which are incorporated in their entireties herein.

FIELD OF THE INVENTION

The present invention relates to a pharmaceutical combination comprising an MDM2 inhibitor and an ERK inhibitor, for use in the treatment of a cancer, particularly in cancers having a mutation in the KRAS pathway. The invention also relates to uses of these compounds in combination for the treatment of such cancers and for preparation of a medicament for the treatment of a cancer; methods of treating a cancer in a subject in need thereof comprising administering to said subject a jointly therapeutically effective amount of said combination; pharmaceutical compositions comprising such combinations; and commercial packages comprising such combinations.

BACKGROUND

The advent of targeted therapies for cancer has increased patient lifespan for various malignancies and helped to appreciate the complexity of tumors through the study of drug resistance mechanisms. The fact that clinical responses to targeted agents are generally incomplete and/or transient results from a multitude of factors that can be broadly put into two classes: toxicities that prevent optimal dosing of drugs and consequently limit target engagement (Brana and Siu 2012, Chapman, Solit et al. 2014), and the ability of cancers to adapt and maintain their proliferative potential against perturbations (Druker 2008, Chandarlapaty 2012, Doebele, Pilling et al. 2012, Duncan, Whittle et al. 2012, Katayama, Shaw et al. 2012, Lito, Rosen et al. 2013, Sullivan and Flaherty 2013, Solit and Rosen 2014). Combinations of drugs can address both these factors by improving overall efficacies and at the same time targeting tumor robustness and complexity to counter resistance (Robert, Karaszewska et al. 2015, Turner, Ro et al. 2015). However, it is not yet clear how many drugs are required and which processes or which combinations of pathways need to be targeted in combination to overcome cancer. But it has been found that in certain cases, combinations of two or more drugs (Bozic, Reiter et al. 2013) can treat cancers more effectively and can combat cancers that mutate and adapt after exposure to a single agent, effectively developing resistance to one therapeutic.

In spite of numerous treatment options for patients with specific types of cancer, there remains a need for effective and safe combination therapies that can be administered for the effective long-term treatment of cancer and for treatment of cancers that possess or tend to develop resistance to single-agent therapies.

SUMMARY

It is an object of the present invention to provide a medicament to improve treatment of a cancer, in particular to improve treatment of cancer through inhibition of cell growth (proliferation) and induction of apoptosis. It is an object of the present invention to provide novel combination therapies that synergize to more effectively reduce proliferation and/or induce apoptosis of tumor cells, and to provide greater anticancer effects, including tumor growth inhibition.

Mouse double minute 2 homolog (MDM2), also known as E3 ubiquitin protein ligase Mdm2, is a negative regulator of tumor protein p3 (p53). Binding of MDM2 to p53 promotes degradation of p53, which is a key regulatory mechanism keeping levels of p53 low in healthy, unstressed cells. The protein p53 has numerous functions in cells, including that of tumor suppressor. In normal, unstressed cells, levels of p53 are low, but if the level of p53 increases, it can become activated and cause a number of cellular changes. In stressed or damaged cells, p53 increases and gets activated by phosphorylation: activated p53 can limit damage to the cell, such as by triggering DNA repair, or it can induce apoptosis, resulting in elimination of the damaged cell. Inhibitors of MDM2 (or Mdm2) are compounds that interfere with binding of MDM2 with p53. Since disruption of the interaction of MDM2 with p53 leads to build-up of p53, and high levels of p53 can cause various effects including cell death, inhibitors of MDM2 can potentially stop tumor growth and even kill tumor cells. Indeed, at least seven inhibitors of MDM2 had entered clinical trials for treating various cancers by 2015. Zhao, et al., *J. Med. Chem.* 58(3), 1038-52 (2015). These compounds are expected to be especially useful to treat tumors that overexpress MDM2, e.g. some liposarcomas, glioblastomas and leukemias, and tumors carrying wild-type p53. Tumors with mutations in p53 may be less sensitive to MDM2 inhibitors if the mutations reduce the ability of the MDM2 inhibitor to disrupt binding of MDM2 to the mutated p53.

MDM2 inhibitors and ERK inhibitors demonstrate useful anticancer activity as separate monotherapies. Surprisingly, it has now been found that using an MDM2 inhibitor in combination with an ERK inhibitor can provide synergistic anticancer activity as demonstrated in xenograft models.

Thus in one aspect, the invention provides a pharmaceutical combination comprising
  (a) an MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one ("Compound A" or "COMPOUND A"),

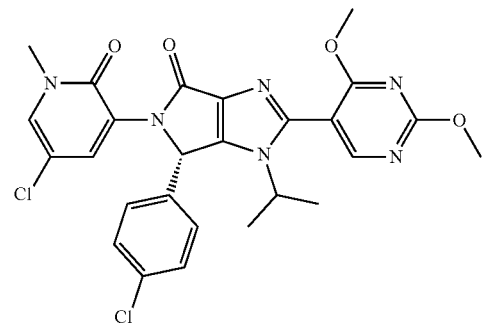 [SMILES: COc1ncc(-c2nc3c(n2C(C)C)[C@H](c2ccc(Cl)cc2)N(c2cc(Cl)cn(C)c2=O)C3=O)c(OC)n1]

which is disclosed in WO2013/111105, or a pharmaceutically acceptable salt thereof; and
  (b) an ERK inhibitor selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide ("Compound B" or "COMPOUND B"); 4-(3-amino-6-((1S,3S,4S)-3- fluoro-4-hydroxycyclohexyl)pyrazin-2-yl)-2-fluoro-N—((S)-1-(3-fluoro-5-iodophenyl)-2-hydroxyethyl) benzamide; and (S)-4-(5-chloro-2-(isopropylamino) pyridin-4-yl)-N-(1-(3-chlorophenyl)-2-hydroxyethyl)-1H-pyrrole-2-carboxamide (BVD-523); and the pharmaceutically acceptable salts of these compounds. Compound A (also referred to herein as "COMPOUND A") is also known by the alternative name of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one.

The combinations of the invention can be practiced with a variety of ERK inhibitors. A preferred ERK inhibitor for use in the combinations and methods of the invention is Compound B (also referred to herein as "COMPOUND B") which is 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide:

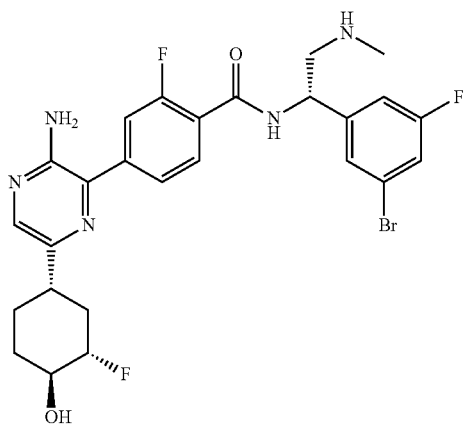 [SMILES: CNC[C@@H](NC(=O)c1ccc(-c2nc([C@H]3CC[C@H](O)[C@@H](F)C3)cnc2N)cc1F)c1cc(F)cc(Br)c1]

This compound is an inhibitor of ERK 1 and ERK 2. The compound is disclosed and its preparation described in published PCT patent application WO2015/066188. In some embodiments, this compound is used as its hydrochloride salt.

Another preferred ERK inhibitor for use in the methods and compositions of the invention is 4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide:

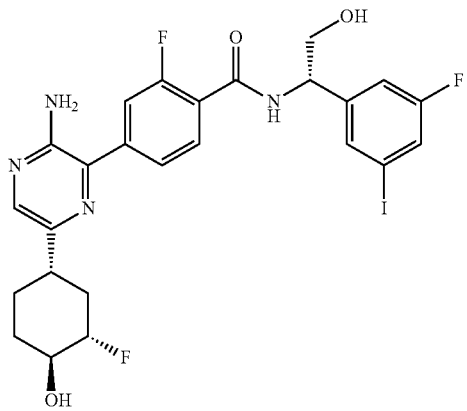 [SMILES: Nc1ncc([C@H]2CC[C@H](O)[C@@H](F)C2)nc1-c1ccc(C(=O)N[C@H](CO)c2cc(F)cc(I)c2)c(F)c1]

This compound is an inhibitor of ERK 1 and ERK 2. The compound is disclosed and its preparation described in published PCT patent application WO2015/066188.

Another ERK inhibitor that can be used in the methods of the invention is BVD-523, also known as ulixertinib, which is (S)-4-(5-chloro-2-(isopropylamino)pyridin-4-yl)-N-(1-(3-chlorophenyl)-2-hydroxyethyl)-1H-pyrrole-2-carboxamide:

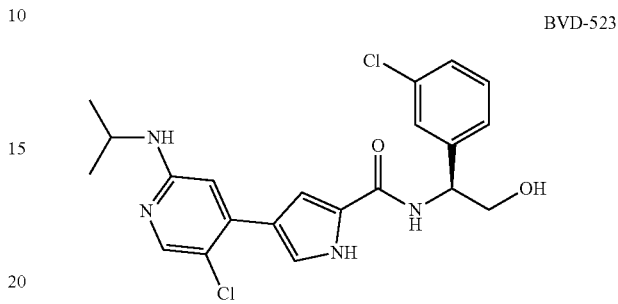

BVD-523

In a preferred embodiment, there is also provided a pharmaceutical combination comprising:
(a) an MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof, and
(b) an ERK inhibitor which is 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide, or a pharmaceutically acceptable salt thereof.

Also provided are:
an MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof, for use in treating cancer in combination with an ERK inhibitor selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino) ethyl)-2-fluorobenzamide; 4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide; and (S)-4-(5-chloro-2-(isopropylamino)pyridin-4-yl)-N-(1-(3-chlorophenyl)-2-hydroxyethyl)-1H-pyrrole-2-carboxamide, or a pharmaceutically acceptable salt of one of these compounds;
an ERK inhibitor selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino) ethyl)-2-fluorobenzamide;
4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide; and (S)-4-(5-chloro-2-(isopropylamino)-pyridin-4-yl)-N-(1-(3-chlorophenyl)-2-hydroxyethyl)-1H-pyrrole-2-carboxamide, or a pharmaceutically acceptable salt of one of these compounds, for use in treating cancer in combination with an MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof;

an MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof, for use in treating cancer by co-administration with an ERK inhibitor selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide; 4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide; and (S)-4-(5-chloro-2-(isopropylamino)pyridin-4-yl)-N-(1-(3-chlorophenyl)-2-hydroxyethyl)-1H-pyrrole-2-carboxamide, or a pharmaceutically acceptable salt of one of these compounds; and an ERK inhibitor selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide;

4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide; and (S)-4-(5-chloro-2-(isopropylamino)pyridin-4-yl)-N-(1-(3-chlorophenyl)-2-hydroxyethyl)-1H-pyrrole-2-carboxamide, or a pharmaceutically acceptable salt of one of these compounds, for use in treating cancer by co-administration with an MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof.

In another aspect, the present invention relates to a pharmaceutical composition comprising the pharmaceutical combination of the invention and at least one pharmaceutically acceptable carrier.

In one aspect, the present invention relates to the pharmaceutical combination or the pharmaceutical composition of the invention for use as a medicine.

In another aspect, the present invention relates to the pharmaceutical combination or the pharmaceutical composition of the invention for use in the treatment of cancer.

In another aspect, the invention provides the use of to the pharmaceutical combination of the invention for the preparation of a medicament for the treatment of a cancer.

In yet another aspect, the present invention relates to a method for treating cancer in a subject in need thereof comprising administering to the subject a therapeutically effective amount of a pharmaceutical combination of the present invention, or the pharmaceutical composition of the present invention.

Specifically, the present invention provides the following aspects and specific embodiments, respectively alone or in combination, as listed in the claims below.

Cancers to be treated by the combination of the invention are listed below. The combinations of this invention are particularly useful for treatment of subjects having cancer, e.g. melanoma, that comprises at least one KRAS mutation and/or at least one BRAF mutation.

DETAILED DESCRIPTION OF THE INVENTION

Figure 1:
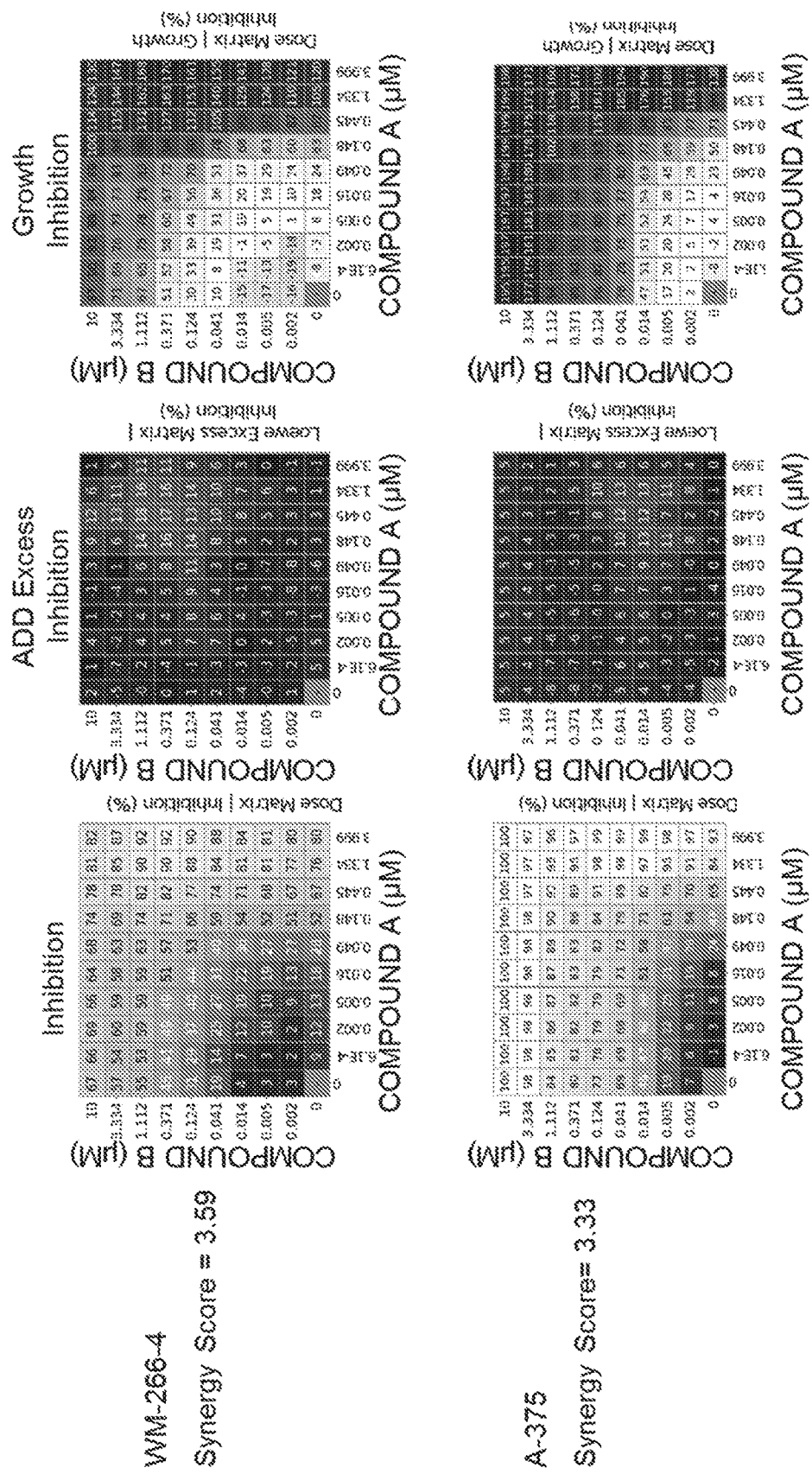
FIG. 1: In vitro results showing cell growth inhibition activity of combinations of (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one (Compound A) and 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide (Compound B).

In one aspect, the present invention relates to a pharmaceutical combination comprising an MDM2 inhibitor used in combination with an ERK inhibitor, where the two compounds can be administered separately, sequentially or together, including as a single pharmaceutical composition. It provides methods for treating cancers using an MDM2 inhibitor in combination with an ERK inhibitor, and provides specific MDM2 and ERK inhibitors for use in these combinations and methods.

It has been found that the combinations of the invention can be used to efficiently treat cancers. In particularly, it has been determined that the combination can be used to treat cancer due to a synergistic effect in inhibition of cell proliferation and/or induction of apoptosis that results from use in combination of the MDM2 inhibitor and the ERK inhibitor. Thus the invention allows use of a lower dosage of one or both compounds being administered to a subject treated with the combinations of the invention, or it produces a greater therapeutic benefit than would have been expected based on effectiveness of the separate compounds.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, patients, cancers and the like, this is taken to mean also a single compound, patient, or the like.

The term "synergistic effect" as used herein refers to action of two therapeutic agents such as, for example, at least one MDM2 inhibitor compound of the present invention and at least one ERK inhibitor compound of the present invention, producing an effect, for example, slowing the progression of a proliferative disease, particularly cancer, or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of a drug combination. The corresponding graphs associated with the equations referred to above are the concentration-effect curve, isobologram curve and combination index curve, respectively.

In particular, it has been demonstrated that combined inhibition of MDM2 and ERK in TP53 wild-type melanoma cell lines provides synergistic activity superior to that expected from the added activities of the inhibitors when used as separate single-agent therapeutics. Thus, the combinations of the present invention provide an effective therapy option capable of improving responses compared to each of the single agents and can lead to more durable responses in the clinic than would have been expected based on the single-agent activities.

The term "MDM2 inhibitor" or "HDM2 inhibitor" or "Mdm2 inhibitor" as used herein, refer to any compound inhibiting the HDM2/p53 (Mdm2/p53) interaction association. HDM2 (Human homolog of murine double minute 2) is a negative regulator of p53. Mdm2 inhibitors are useful in pharmaceutical compositions for human or veterinary use where inhibition of Mdm2/p53 association is indicated, e.g., in the treatment of tumors and/or cancerous cell growth. In particular, Mdm2 inhibitors are useful in the treatment of human cancer, since the progression of these cancers may be at least partially dependent upon overriding the "gatekeeper" function of p53, for example the overexpression of Mdm2.

According to the present invention, the Mdm2 inhibitor is the compound
(6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof.

The MDM2 inhibitor is also referred to herein as Compound A. This Mdm2 inhibitor belongs to a novel class of imidazopyrrolidinone compounds, and shows potent inhibition of the MDM2/p53 interaction (this term including in particular Hdm2/p53 interaction). In particular, this compound acts as an inhibitor of MDM2 interaction with p53 by binding to MDM2. The MDM2 inhibitor (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one,

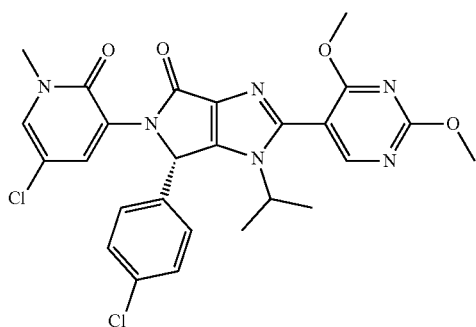 [SMILES: COc1ncc(-c2nc3c(n2C(C)C)[C@H](c2ccc(Cl)cc2)N(c2cc(Cl)cn(C)c2=O)C3=O)c(OC)n1]

is described in Example 102 of WO2013/111105, which is hereby incorporated by reference in its entirety.

The crystalline forms of (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one are described as EX6, EX7 and EX8 in WO2013/111105. The invention encompasses succinic acid co-crystal of the (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one compound. The compound can be also be in a form of an ethanol solvate.

CGM097 is an MDM2 inhibitor and is (S)-1-(4-Chlorophenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one and is described in Example 106 of WO2011/076786

(II)

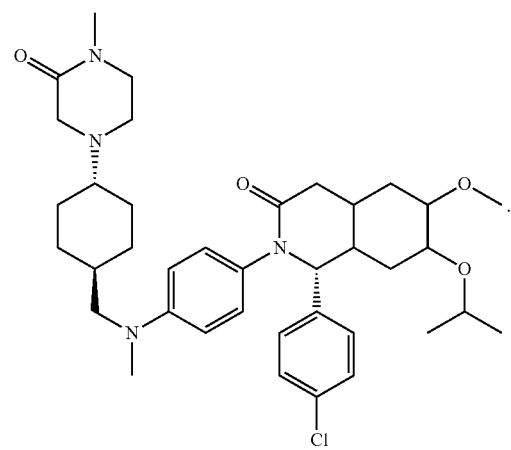

WO2012/066095 describe the bisuphate salt and crystalline forms thereof.

In one embodiment, the ERK inhibitor for use in the compositions and methods of the invention is prepared for administration via oral delivery, and may be used as its hydrochloride salt. In some embodiments, the compound or its HCl salt is simply encapsulated in a pharmaceutically acceptable container such as a hard or soft gelcap for oral administration. The gelcaps can be produced in a variety of dosages for flexible administration; for example, gelcaps can be prepared containing about 5 mg, about 20 mg, about 50 mg, or about 100 mg of Compound B or its HCl salt.

The term "pharmaceutically acceptable salts" refers to salts that retain the biological effectiveness and properties of the compound and which typically are not biologically or otherwise undesirable. The compound may be capable of forming acid addition salts by virtue of the presence of an amino group.

Unless otherwise specified, or clearly indicated by the text, reference to therapeutic agents useful in the pharmaceutical combination of the present invention includes both the free base of the compounds, and all pharmaceutically acceptable salts of the compounds.

The term "combination" or "pharmaceutical combination" is defined herein to refer to either a fixed combination in one dosage unit form, a non-fixed combination or a kit of parts for the combined administration where the therapeutic agents may be administered together, independently at the same time or separately within time intervals, which preferably allows that the combination partners to show a cooperative, e.g. synergistic effect. Thus, the single compounds of the pharmaceutical combination of the present invention could be administered simultaneously or sequentially.

Furthermore, the pharmaceutical combination of the present invention may be in the form of a fixed combination or in the form of a non-fixed combination.

The term "fixed combination" means that the therapeutic agents, e.g., the single compounds of the combination, are in the form of a single entity or dosage form.

The term "non-fixed combination" means that the therapeutic agents, e.g., the single compounds of the combination, are administered to a patient as separate entities or dosage forms either simultaneously or sequentially with no specific time limits, wherein preferably such administration provides therapeutically effective levels of the two therapeutic agents in the body of the subject, e.g., a mammal or human in need thereof.

The pharmaceutical combinations can further comprise at least one pharmaceutically acceptable carrier. Thus, the present invention relates to a pharmaceutical composition comprising the pharmaceutical combination of the present invention and at least one pharmaceutically acceptable carrier.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Generally, the term "pharmaceutical composition" is defined herein to refer to a mixture or solution containing at least one therapeutic agent to be administered to a subject, e.g., a mammal or human. The present pharmaceutical combinations can be formulated in a suitable pharmaceutical composition for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units. The pharmaceutical composition may contain, from about 0.1% to about 99.9%, preferably from about 1% to about 60%, of the therapeutic agent(s). One of ordinary skill in the art may select one or more of the aforementioned carriers with respect to the particular desired properties of the dosage form by routine experimentation and without any undue burden. The amount of each carriers used may vary within ranges conventional in the art. The following references disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2003). These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet. Clearly, the pharmaceutical combinations of the present invention can be used to manufacture a medicine.

The present invention relates to such pharmaceutical combinations or pharmaceutical compositions that are particularly useful as a medicine.

Specifically, the combinations or compositions of the present invention can be applied in the treatment of cancer.

The present invention also relates to use of pharmaceutical combinations or pharmaceutical compositions of the present invention for the preparation of a medicament for the treatment of a cancer, and to a method for treating cancer in a subject in need thereof comprising administering to the subject a therapeutically effective amount of a pharmaceutical combination according to the present invention, or the pharmaceutical composition according to the present invention.

The term "treatment" as used herein comprises a treatment relieving, reducing or alleviating at least one symptom in a subject, increasing progression-free survival, overall survival, extending duration of response or delaying progression of a disease. For example, treatment can be the diminishment of one or several symptoms of a disorder or complete eradication of a disorder, such as cancer. Within the meaning of the present invention, the term "treatment" also denotes to arrest, delay the onset (i.e., the period prior to clinical manifestation of a disease) and/or reduce the risk of developing or worsening a disease in a patient, e.g., a mammal, particularly the patient is a human. The term "treatment" as used herein comprises an inhibition of the growth of a tumor incorporating a direct inhibition of a primary tumor growth and/or the systemic inhibition of metastatic cancer cells.

A "subject," "individual" or "patient" is used interchangeably herein, which refers to a vertebrate, preferably a mammal, more preferably a human. Mammals include, but are not limited to, mice, simians, humans, farm animals, sport animals, and pets.

The term "a therapeutically effective amount" of a compound (e.g. chemical entity or biologic agent) of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one embodiment a therapeutically effective amount in vivo may range depending on the route of administration, between about 0.1-500 mg/kg, or between about 1-100 mg/kg.

The optimal dosage of each combination partner for treatment of a cancer can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art. The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

A therapeutic amount or a dose of (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one may range between 100 and 1500 mg every three weeks, particularly between 100 and 800 mg every three weeks, or between 50 and 600 mg daily, when administered per os. A therapeutic amount or a dose of (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one can be 400 mg, more preferably is 300 mg for daily administration for the first 21 days of every 28 day cycle. Alternatively, a total therapeutic amount or a total dose of (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one is 560 mg per cycle (40 mg qd 2 wks on/2 wks off, or 80 mg qd 1 wk on/3 wks off). Moreover, the dosage for use in the combinations of the invention will typically be lower than those above, which are appropriate for use of this compound as a single agent. Accordingly, a dosage between 100 and 500 mg every three weeks may be suitable, or a dosage of 50 to 400 mg daily may be suitable for oral administration, and lower dosages such as 200 mg or 300 mg daily for the first 21 days of a 28-day cycle may be used. Intravenous doses would need to be lowered accordingly.

It is understood that each therapeutic agent may be conveniently administered, for example, in one individual dosage unit or divided into multiple dosage units. It is further understood that that each therapeutic agent may be conveniently administered in doses once daily or doses up to four times a day.

The term "cancer" is used herein to mean a broad spectrum of tumors, in particular solid tumors. Examples of such tumors include, but are not limited to a benign or malignant tumor of the lung (including small cell lung cancer and non-small-cell lung cancer), bronchus, prostate, breast (including sporadic breast cancers and sufferers of Cowden disease), pancreas, gastrointestinal tract, colon, rectum, colon carcinoma, colorectal cancer, thyroid, liver, biliary tract, intrahepatic bile duct, hepatocellular, adrenal gland, stomach, gastric, glioma, glioblastoma, endometrial, kidney, renal pelvis, bladder, uterus, cervix, vagina, ovary, multiple myeloma, esophagus, neck or head, brain, oral cavity and pharynx, larynx, small intestine, a melanoma, villous colon adenoma, a sarcoma, a neoplasia, a neoplasia of epithelial character, a mammary carcinoma, basal cell carcinoma, squamous cell carcinoma, actinic keratosis, polycythemia vera, essential thrombocythemia, a leukemia (including acute myelogenous leukemia, chronic myelogenous leukemia, lymphocytic leukemia, and myeloid leukemia), a lymphoma (including non-Hodgkin lymphoma and Hodgkin's lymphoma), myelofibrosis with myeloid metaplasia, Waldenstroem disease, and Barret's adenocarcinoma.

Preferably, the cancer is melanoma, liposarcoma, glioblastoma, neuroblastoma, colorectal cancer, lymphoma or leukemia. In a preferred embodiment the cancer is melanoma. In one embodiment, the present invention relates to melanoma having a mutation that confers resistance to a RAF inhibitor, such as V600E mutation of BRAF. In some such embodiments, the melanoma is further characterized by a wild-type p53.

The combination is expected to achieve superior effects in functional p53 or p53 wild-type cancers. The TP53 gene is one of the most frequently mutated genes in human cancers. Thus, tumor suppressor p53 is functionally impaired by mutation or deletion in nearly 50% of human cancers. In the remaining human cancers, p53 retains wild-type status but its function is inhibited by its primary cellular inhibitor, the murine double minute 2 (Mdm2, MDM2; HDM2 (human homolog of murine double minute 2)). Mdm2 is a negative regulator of the p53 tumor suppressor. Mdm2 protein functions both as an E3 ubiquitin ligase, that leads to proteasomal degradation of p53, and an inhibitor of p53 transcriptional activation. Often Mdm2 is found amplified in p53 wild-type tumors. Because the interaction between Mdm2 and p53 is a primary mechanism for inhibition of the p53 function in cancers, which are retaining wild-type p53, the combination of the present invention comprising the MDM2 inhibitor is particularly useful for treatment of functional p53 or p53 wild-type cancers.

In addition, the efficacy of the combination is expected to be increased in cancer, which is characterized by one or more of NRAS or KRAS mutation and/or BRAF mutation.

Patients with melanoma harboring KRAS or BRAF mutations are generally associated with a poor prognosis (Arrington, Heinrich et al. 2012, Safaee Ardekani, Jafarnejad et al. 2012). The combinations of this invention are particularly useful for treatment of subjects having melanoma that comprises at least one KRAS mutation and/or at least one BRAF mutation.

Examples of BRAF mutations include, but not limited to V600E, R461I, I462S, G463E, G463V, G465A, G465E, G465V, G468A, G468E, N580S, E585K, D593V, F594L, G595R, L596V, T598I, V599D, V599E, V599K, V599R, V600K, A727V. Most of these mutations are clustered to two regions: the glycine-rich P loop of the N lobe and the activation segment and flanking regions V600E mutation has been detected in a variety of cancers, and is due to a substitution of thymine with adenine at nucleotide 1799. This leads to valine (V) being substituted for by glutamate (E) at codon 600 (now referred to as V600E).

In particular, the combinations of the invention may be useful in treating BRAF mutant melanoma, e.g. BRAF-V600E mutant melanoma. These melanoma may also be resistant to vemurafenib.

The following Examples illustrates the invention described above, but is not intended to limit the scope of the invention in any way. Other test models known as such to the person skilled in the pertinent art can also determine the beneficial effects of the claimed invention.

EXAMPLES

The following examples illustrate synergistic activity when an ERK inhibitor is used in combination with an MDM2 inhibitor to treat cancers having BRAF mutations. Example 1 illustrates synergy in vitro, and Example 2 illustrates synergy in an in vivo xenograft model using a different combination of inhibitors of ERK and MDM2.

Example 1: The In Vitro Effects of Combining the Mdm2 Inhibitor COMPOUND A with the ERK Inhibitor COMPOUND B on Proliferation in Melanoma Cell Lines WM-266-4 and A-375

This study was designed to explore the in vitro effect of combining an MDM2 inhibitor with an ERK inhibitor on melanoma models expressing BRAF mutations. The MDM2 inhibitor (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one ("Compound A") was tested in combination with the ERK inhibitor 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide ("Compound B") at a range of concentrations. Two BRAF mutated melanoma cell lines were tested, WM-266-4 and A-375.

Compounds were dissolved in 100% DMSO (Sigma, Catalog #D2438-50ML) at a stock concentration of 10 mM and stored at −20° C. until use. For combinations, compounds were diluted in 3-fold serial dilutions in Dilux dilution reservoirs (Chemglass Life Sciences, Catalog #CLS-3796-001). COMPOUND A was used over a concentration range of 0.0-4.0 µM. COMPOUND B was used over a concentration range of 0.0-10.0 µM.

Cell lines were purchased from the American Type Culture Collection. A-375 cells were cultured in Dulbecco's Modified Eagle Medium (Life Technologies, Catalog #11995-065) and WM-266-4 cells were cultured in Minimum Essential Medium Alpha (Life Technologies, Catalog #12561-056). Both lines were supplemented with 10% FBS (Seradigm, Catalog #1500-500). All cell lines were determined to be free of mycoplasma contamination by a PCR detection assay performed at Idexx Radil (Columbia, Mo., USA) and authenticated by SNP analysis. Cells were thawed from frozen stocks, expanded through ≥1 passage and grown at 37° C. in 5% $CO_2$. Cells were expanded to T-75 flasks and assessed for viability using a Beckman-Coulter ViCell counter prior to plating. To split and expand cell lines, cells were dislodged from flasks using 0.25% Trypsin-EDTA (Corning Costar, Catalog #25-053-CL).

For combination assays, cells were added to 96-well plates (Corning Costar, Catalog #3904) at a final volume of 80 µL per well and at density of 2500 cells (for A-375) or 4000 cells (for WM-266-4) per well. After plating for 12-24 hours, 10 µL of each compound dilution series was transferred to plates in triplicate, resulting in the compound concentration ranges specified above. Additionally a day zero plate was assayed at this time using the CellTiter-Glo® Luminescent Cell Viability Assay, as described below. After 72 hours of compound treatment, the effects of compounds on cell proliferation were determined using the CellTiter-Glo™ Luminescent Cell Viability Assay (Promega, Catalog #G7573). This is a homogeneous method to determine the number of viable cells in culture based on quantitation of the ATP present, which signals the presence of metabolically active cells. The method is described in detail in the Technical Bulletin, TB288 Promega. Briefly, 100 µl of CTG Reagent was added to plates and plates were incubated for 20-30 minutes on an orbital shaker. Plates were then read on the Perkin Elmer Victor™ X4 plate reader.

The percent growth inhibition, excess inhibition and growth inhibition were calculated using Combo Module software using the Loewe synergy model (as described in Lehar et al. 2009), which measures the effect on growth above what would be expected if two drugs behaved in a dose additive manner. Positive numbers represent areas of increasing synergy. The percentage of growth inhibition relative to DMSO is displayed in the panel labelled "Inhibition." The amount of inhibition in excess of the expected amount is in the panel labelled "ADD Excess Inhibition." The amount of inhibition normalized to day zero is displayed in the panel labelled "Growth Inhibition." Concentrations of COMPOUND A are shown along the bottom row from left to right and increasing concentrations of COMPOUND B along the left most column from bottom to top. All remaining points in the grids display results from a combination of the two inhibitors that correspond to the single agent concentrations denoted on the two axes. Absolute AC50 was determined by finding the compound concentration where the calculated curve crosses the 50% activity mark. Absolute AC50 and synergy score were calculated in Combo module software as described in Lehar et al. (2009).

Synergy Score
SS~0→Dose Additive
SS>2→Synergy
SS>1→Weak Synergy

FIG. 1 shows matrices for inhibition, Loewe (ADD) excess inhibition and growth inhibition for COMPOUND B combinations with COMPOUND A in melanoma cell lines.

The table below shows single agent IC50 values for each compound and synergy score measurements for the combination of COMPOUND A+COMPOUND B using the method described in Lehar J, Krueger A S, Avery W, et al. (2009) to assess synergy. Synergistic drug combinations tend to improve therapeutically relevant selectivity. *Nat Biotechnol* 27: 659-666). Interactions were deemed synergistic when scores ≥2.0 were observed. The data demonstrate synergistic activity between Compound A and Compound B in two different melanoma cell lines that contain BRAF resistant mutations.

| Cell Line | Compound A Absolute AC50 (µM) | Compound B Absolute AC50 (µM) | Synergy Score |
|---|---|---|---|
| WM-266-4 | 0.156 | 0.616 | 3.59 |
| A-375 | 0.195 | 0.0205 | 3.33 |

Example 2: Activity in Xenografts of a BRAF Inhibitor-Resistant Melanoma

A xenograft model derived from a patient whose melanoma progressed despite treatment with vemurafenib, a BRAF inhibitor, was established in immune-deficient mice (Hidalgo et al., 2014). The xenograft tissue was determined to have a BRAF V600E mutation and wild type p53, and also an additional unidentified activating MEK mutation. A biomarker signature suggested the tissue would be sensitive to p53 re-activation. As expected, mice with this xenograft did not respond to a BRAF inhibitor.

Figure 2A:
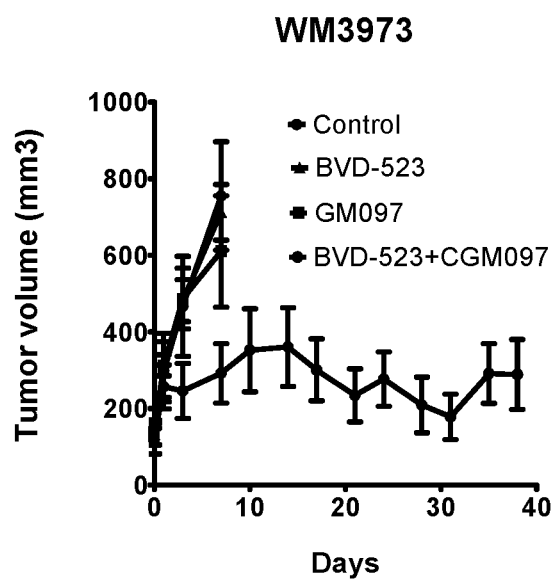
FIG. 2A: Patient Derived Xenograft (PDX) model from a BRAF-V600E patient relapsed on vemurafenib (Progression Free Survival (PFS) 46 weeks, best response stable disease) that had an additional activating MEK mutation, TP53 WT, and a biomarker signature indicating sensitivity to p53 re-activation. PDX tumor xenografts in mice (n=10/group) were treated with the ERK inhibitor BVD-523 50 mg/kg twice daily oral gavage, the MDM2 inhibitor CGM097 100 mg/kg once daily oral gavage, or the combination of both. CGM097 is (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one.

Mice having this xenograft were treated with CGM097 (100 mg/kg once per day by oral gavage), or BVD-523 (50 mg/kg twice daily by oral gavage), or both together (10 animals per treatment). FIG. 2A shows averaged tumor growth curves for each treatment. Rate of tumor growth in animals receiving the single-agent treatments did not differ much from controls. However, the combination of CGM097 plus BVD-523 largely stopped tumor growth over a period of 38 days. Thus treatment with BVD-523 and CGM097 together produced synergistic effects, resulting in stable disease over this period.

Figure 2B:
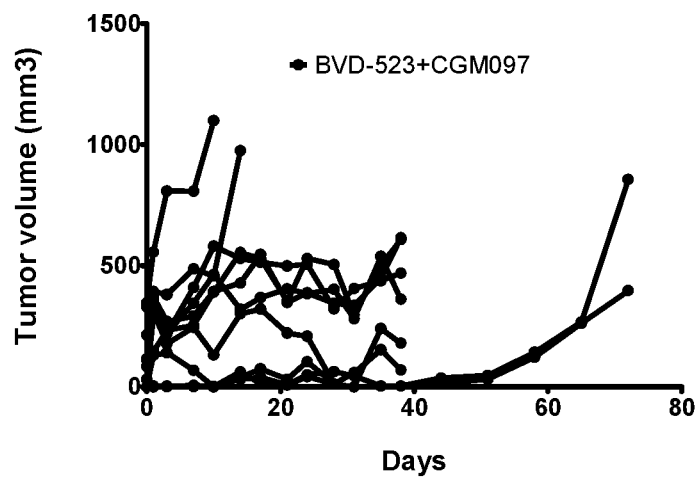
FIG. 2B: Single mouse growth curves of the BVD-523+CGM097 treated group highlighting the heterogeneity of response in PDX models. While the majority of tumors showed stable disease, two mice had early relapse and two mice had complete responses (CR). Dosing was stopped on day 38 for the whole group and the two CR mice showed regrowth of residual disease.

FIG. 2B shows tumor growth curves for each individual animal in the combination treatment group. Two of the animals did not respond well to the combination treatment, but 6 exhibited stable disease out to 38 days, and two others exhibited marked tumor shrinkage, so 8 of 10 animals responded to the combination. Treatment was stopped at day 38 (arrow in FIG. 2B), and tumor regrowth occurred in both of the animals whose tumors had nearly disappeared during treatment.

REFERENCES CITED HEREIN

Arrington, A. K., E. L. Heinrich, W. Lee, M. Duldulao, S. Patel, J. Sanchez, J. Garcia-Aguilar and J. Kim (2012). "Prognostic and predictive roles of KRAS mutation in colorectal cancer." Int J Mol Sci 13(10): 12153-12168.

Bozic, I., J. G. Reiter, B. Allen, T. Antal, K. Chatterjee, P. Shah, Y. S. Moon, A. Yaqubie, N. Kelly, D. T. Le, E. J. Lipson, P. B. Chapman, L. A. Diaz, Jr., B. Vogelstein and M. A. Nowak (2013). "Evolutionary dynamics of cancer in response to targeted combination therapy." Elife 2: e00747.

Brana, I. and L. L. Siu (2012). "Clinical development of phosphatidylinositol 3-kinase inhibitors for cancer treatment." BMC Med 10: 161.

Chandarlapaty, S. (2012). "Negative feedback and adaptive resistance to the targeted therapy of cancer." Cancer Discov 2(4): 311-319.

Chapman, P. B., D. B. Solit and N. Rosen (2014). "Combination of RAF and MEK inhibition for the treatment of BRAF-mutated melanoma: feedback is not encouraged." Cancer Cell 26(5): 603-604.

Chatterjee, M. S., J. E. Purvis, L. F. Brass and S. L. Diamond (2010). "Pairwise agonist scanning predicts cellular signaling responses to combinatorial stimuli." Nat Biotechnol 28(7): 727-732.

Chou, T. C. and P. Talalay (1981). "Generalized equations for the analysis of inhibitions of Michaelis-Menten and higher-order kinetic systems with two or more mutually exclusive and nonexclusive inhibitors." Eur J Biochem 115(1): 207-216.

Doebele, R. C., A. B. Pilling, D. L. Aisner, T. G. Kutateladze, A. T. Le, A. J. Weickhardt, K. L. Kondo, D. J. Linderman, L. E. Heasley, W. A. Franklin, M. Varella-Garcia and D.

R. Camidge (2012). "Mechanisms of resistance to crizotinib in patients with ALK gene rearranged non-small cell lung cancer." Clin Cancer Res 18(5): 1472-1482.

Druker, B. J. (2008). "Translation of the Philadelphia chromosome into therapy for CML." Blood 112(13): 4808-4817.

Duncan, J. S., M. C. Whittle, K. Nakamura, A. N. Abell, A. A. Midland, J. S. Zawistowski, N. L. Johnson, D. A. Granger, N. V. Jordan, D. B. Darr, J. Usary, P. F. Kuan, D. M. Smalley, B. Major, X. He, K. A. Hoadley, B. Zhou, N. E. Sharpless, C. M. Perou, W. Y. Kim, S. M. Gomez, X. Chen, J. Jin, S. V. Frye, H. S. Earp, L. M. Graves and G. L. Johnson (2012). "Dynamic reprogramming of the kinome in response to targeted MEK inhibition in triple-negative breast cancer." Cell 149(2): 307-321.

Hidalgo, M. et al. (2014), "Patient-derived xenograft models: an emerging platform for translational cancer research," Cancer Discov. 4, 998-1013.

Katayama, R., A. T. Shaw, T. M. Khan, M. Mino-Kenudson, B. J. Solomon, B. Halmos, N. A. Jessop, J. C. Wain, A. T. Yeo, C. Benes, L. Drew, J. C. Saeh, K. Crosby, L. V. Sequist, A. J. Iafrate and J. A. Engelman (2012). "Mechanisms of acquired crizotinib resistance in ALK-rearranged lung Cancers." Sci Transl Med 4(120): 120ra117.

Lehar, J., A. Krueger, G. Zimmermann and A. Borisy (2008). "High-order combination effects and biological robustness." Mol Syst Biol 4: 215.

Lito, P., N. Rosen and D. B. Solit (2013). "Tumor adaptation and resistance to RAF inhibitors." Nat Med 19(11): 1401-1409.

Robert, C., B. Karaszewska, J. Schachter, P. Rutkowski, A. Mackiewicz, D. Stroiakovski, M. Lichinitser, R. Dummer, F. Grange, L. Mortier, V. Chiarion-Sileni, K. Drucis, I. Kraj soya, A. Hauschild, P. Lorigan, P. Wolter, G. V. Long, K. Flaherty, P. Nathan, A. Ribas, A. M. Martin, P. Sun, W. Crist, J. Legos, S. D. Rubin, S. M. Little and D. Schadendorf (2015). "Improved overall survival in melanoma with combined dabrafenib and trametinib." N Engl J Med 372(1): 30-39.

Safaee Ardekani, G., S. M. Jafarnejad, L. Tan, A. Saeedi and G. Li (2012). "The prognostic value of BRAF mutation in colorectal cancer and melanoma: a systematic review and meta-analysis." PLoS One 7(10): e47054.

Solit, D. B. and N. Rosen (2014). "Towards a unified model of RAF inhibitor resistance." Cancer Discov 4(1): 27-30.

Sullivan, R. J. and K. T. Flaherty (2013). "Resistance to BRAF-targeted therapy in melanoma." Eur J Cancer 49(6): 1297-1304.

Turner, N. C., J. Ro, F. Andre, S. Loi, S. Verma, H. Iwata, N. Harbeck, S. Loibl, C. Huang Bartlett, K. Zhang, C. Giorgetti, S. Randolph, M. Koehler and M. Cristofanilli (2015). "Palbociclib in Hormone-Receptor-Positive Advanced Breast Cancer." N Engl J Med.

The invention claimed is:

1. A pharmaceutical combination comprising:
   (a) a MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof, and
   (b) an ERK inhibitor, or a pharmaceutically acceptable salt thereof, selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide; 4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide; and (S)-4-(5-chloro-2-(isopropylamino)pyridin-4-yl)-N-(1-(3-chlorophenyl)-2-hydroxyethyl)-1H-pyrrole-2-carboxamide (BVD-5).

2. The pharmaceutical combination according to claim 1, wherein the ERK inhibitor is 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide or a pharmaceutically acceptable salt thereof.

3. The pharmaceutical combination according to claim 1, wherein the ERK inhibitor is 4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide or a pharmaceutically acceptable salt thereof.

4. The pharmaceutical combination according to claim 1, wherein the ERK inhibitor is (S)-4-(5-chloro-2-(isopropylamino)pyridin-4-yl)-N-(1-(3-chlorophenyl)-2-hydroxyethyl)-1H-pyrrole-2-carboxamide, or a pharmaceutically acceptable salt thereof.

5. A pharmaceutical combination comprising:
(a) a MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one, or a pharmaceutically acceptable salt thereof, and
(b) an ERK inhibitor which is 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide,
or a pharmaceutically acceptable salt thereof.

6. The pharmaceutical combination according to claim 1, which comprises amounts of the MDM2 inhibitor and the ERK inhibitor that are jointly therapeutically effective.

7. The pharmaceutical combination according to claim 6, wherein the amounts of the MDM2 inhibitor and the ERK inhibitor are jointly therapeutically effective for treatment of a cancer that expresses a BRAF mutation.

8. The pharmaceutical combination according to claim 7, wherein the amounts of the MDM2 inhibitor and the ERK inhibitor are jointly therapeutically effective for treatment of a melanoma that expresses a BRAF mutation.

9. The pharmaceutical combination according to claim 1 for simultaneous or sequential use.

10. The pharmaceutical combination according to claim 1 in the form of a fixed combination.

11. The pharmaceutical combination according to claim 1 in the form of a non-fixed combination.

12. A method to treat melanoma, which comprises administering to a subject in need thereof a therapeutically effective amount of (a) a MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one or a pharmaceutically acceptable salt thereof, and
(b) a therapeutically effective amount of an ERK inhibitor, or a pharmaceutically acceptable salt thereof, selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide; 4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide; and (S)-4-(5-chloro-2-(isopropylamino)pyridin-4-yl)-N-(1-(3-chlorophenyl)-2-hydroxyethyl)-1H-pyrrole-2-carboxamide.

13. The method of claim 12, wherein the therapeutically effective amount of the MDM2 inhibitor and the therapeutically effective amount of the ERK inhibitor are jointly effective to treat a cancer expressing wild type p53.

14. The method of claim 12, wherein the therapeutically effective amount of the MDM2 inhibitor and the therapeutically effective amount of the ERK inhibitor are jointly effective due to synergistic efficacy by the MDM2 inhibitor and the ERK inhibitor.

15. The method of claim 14, wherein the melanoma expresses a BRAF mutation.

16. A pharmaceutical composition comprising:
(a) a MDM2 inhibitor which is (6S)-5-(5-Chloro-1-methyl-2-oxo-1,2-dihydropyridin-3-yl)-6-(4-chlorophenyl)-2-(2,4-dimethoxypyrimidin-5-yl)-1-(propan-2-yl)-5,6-dihydropyrrolo[3,4-d]imidazol-4(1H)-one or a pharmaceutically acceptable salt thereof,
(b) an ERK inhibitor, or a pharmaceutically acceptable salt thereof, selected from 4-(3-amino-6-((1S,3S,4S)-3-fluoro-4-hydroxycyclohexyl)pyrazin-2-yl)-N—((S)-1-(3-bromo-5-fluorophenyl)-2-(methylamino)ethyl)-2-fluorobenzamide; 4-(3-amino-6-((1S,3S,4S)-3-fluoro-4-hydroxycyclohexyl)pyrazin-2-yl)-2-fluoro-N—((S)-1-(3-fluoro-5-iodophenyl)-2-hydroxyethyl)benzamide; and (S)-4-(5-chloro-2-(isopropylamino)pyridin-4-yl)-N-(1-(3-chlorophenyl)-2-hydroxyethyl)-1H-pyrrole-2-carboxamide; and
(c) at least one pharmaceutically acceptable carrier or excipient.

17. The pharmaceutical composition according to claim 16, which comprises amounts of the MDM2 inhibitor and the ERK inhibitor that are jointly therapeutically effective.

* * * * *